United States Patent [19]
Albe et al.

[11] Patent Number: 5,084,910
[45] Date of Patent: Jan. 28, 1992

[54] X-RAY DIFFRACTOMETER SAMPLE HOLDER

[75] Inventors: William R. Albe; Chi-Tang Li, both of Midland, Mich.

[73] Assignee: Dow Corning Corporation, Midland, Mont.

[21] Appl. No.: 628,753

[22] Filed: Dec. 17, 1990

[51] Int. Cl.$^5$ .......................................... G01N 23/207
[52] U.S. Cl. ...................................... 378/75; 378/79; 378/208
[58] Field of Search ...................... 378/70, 71, 73, 75, 378/79-81, 208

[56] References Cited

U.S. PATENT DOCUMENTS

| | | | |
|---|---|---|---|
| 2,495,173 | 1/1950 | Leape | 378/75 |
| 3,148,275 | 9/1964 | Mack | 378/75 |
| 3,307,036 | 2/1967 | Bouvelle | 378/75 |
| 4,078,175 | 3/1978 | Fletcher et al. | 378/79 |

Primary Examiner—Janice A. Howell
Assistant Examiner—David P. Porta
Attorney, Agent, or Firm—Roger E. Gobrogge

[57] ABSTRACT

The present invention relates to a sample holder to be used with an x-ray powder diffractometer. One of the novel features resides in the fact that the sample holder is made of single crystal silicon grown in the [100] direction. This sample holder may have a cavity therein for holding a powder sample.

18 Claims, 1 Drawing Sheet

X-RAY DIFFRACTOMETER SAMPLE HOLDER

BACKGROUND

The present invention relates to a sample holder to be used with an x-ray powder diffractometer. One of the novel aspects herein resides in the fact that the sample holder is made of single crystal silicon grown in the [100] direction. This sample holder may also have a cavity therein for holding the powder sample.

X-ray powder diffractometry is a commonly used analytical technique for determining qualitative and quantitative phase data about a substance. Fundamentally, the procedure involves directing a small beam of monochromatic x-rays onto a polycrystalline specimen and then recording the resultant pattern of diffracted x-rays as diffraction signal peaks on film or with a counter tube. Since different substances produce unique diffraction patterns because of their atomic arrangement, this technique serves as a 'fingerprint' for identification of unknown materials.

The specimen to be analyzed in the above manner is placed on a sample holder which is then inserted into the diffractometer. The design of such a holder is important both for ease of use and for obtaining the best analytical results. For instance to obtain good results the holder should be made of a material which doesn't produce strong background signal intensity which may hide little peaks caused by the sample. Similarly, if the holder is made of a material which does produce large diffraction peaks, these peaks should be in an area of the diffraction pattern which doesn't interfere with interpretation of the diffraction peaks derived from the sample. For ease of use, the holder should be easy to clean, weigh and align, and it should be cost effective to manufacture.

Because of the above requirements, various sample holders have been designed and manufactured from aluminum, plastic and quartz. Each of these holders, however, has been found to have drawbacks. Aluminum holders, for instance, are relatively inexpensive to manufacture and they provide diffraction patterns with low background signal intensity. However, such holders do produce diffraction peaks in an area of the diffraction pattern which may interfere with interpretation of results. Similarly, plastic holders are inexpensive to manufacture and their diffraction pattern doesn't contain sharp diffraction peaks which interfere with analysis of the results. These holders do, however, produce diffraction patterns with relatively high background signal intensity and they are often difficult to clean. Finally, quartz holders are advantageous in that they produce a good diffraction pattern with low background signal intensity and few diffraction peaks which interfere with analysis of the results. Quartz holders, however, are fragile and very expensive to manufacture into the desired shape and form.

The present inventors have now discovered a sample holder which avoids the above problems associated with the prior art.

DETAILED DESCRIPTION OF THE INVENTION

The present invention is based on the discovery that an x-ray powder diffractometer sample holder made of single crystal silicon grown in the [100] direction is inexpensive, very easy to use and provides desirable diffraction pattern results.

The sample holder of this invention is generally used by placing it into a sample holder base and then inserting the loaded sample holder base into the x-ray powder diffractometer. The powder specimen to be analyzed may be placed in the sample holder either prior to introducing the holder into the base or after the holder is within the base.

Figure 1:
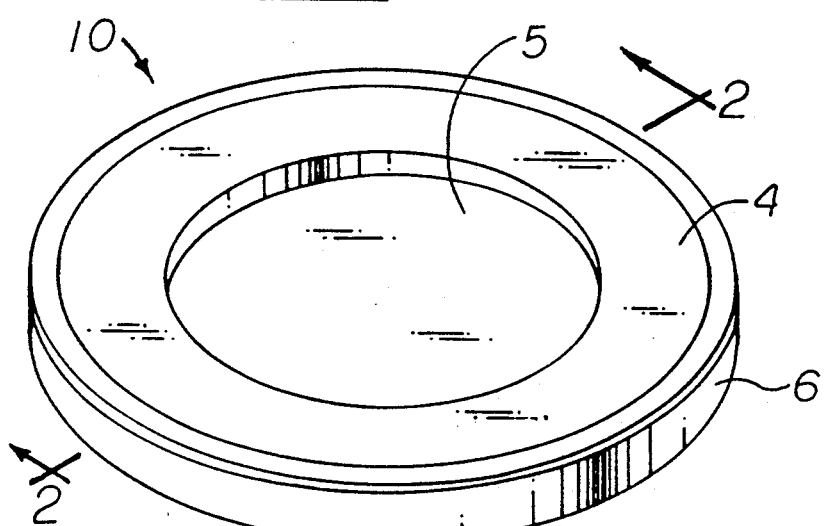
FIG. 1 is a top perspective view of a sample holder of this invention in a typical sample holder base.

FIG. 1 is a top perspective view of a representative sample holder of this invention (10) in a representative sample holder base ((6) being the upper portion of said base with a cavity therein for holding the sample holder and (7) being a stem of said base). The sample holder base as depicted therein is designed to simply fit into a given x-ray powder diffractometer and support the sample holder in a suitable location which allows the device to analyze the specimen. Since such bases can vary depending on the and/or manufacturer of the diffractometer different size or shape sample holders than that depicted in the Figure may be required and are contemplated to be within the scope of this invention. In light of such variation, however, the discussion below will be limited to sample holders which fit into the base of a Phillips TM x-ray powder diffractometer as shown in FIG. 1 (especially since these holders also fit into the sample holder bases which are used in a Siemens TM diffractometer). Such bases support a circular sample holder with a diameter of about 1 inch and a thickness of about 0.043 inches.

As set forth above. FIG. 1 shows a sample holder (10) of this invention resting in a sample holder base. This sample holder comprises a circular disk manufactured from single crystal silicon grown in the [100] direction having a cavity (5) therein to hold the powder sample. Several methods of growing this type of single crystal silicon, such as the Teal-Little and floating-zone methods, are well known in the art. Such methods generally result in the production of long rods of the silicon from which slices of the appropriate thickness are cut, lapped and polished. Various commercial sources of such single crystal rods or slices are readily available. Particularly preferred herein, however, is the use of silicon wafers (slices) which are mass produced for the electronics industry in a variety of thicknesses. These wafers are advantageous in that they have a polished surface and are relatively inexpensive.

The above silicon wafer (slice) is then cut to the desired sample holder size by cutting or machining techniques well known in the art. For the base described above in FIG. 1, a circular disk approximately 1 inch in diameter is cut and a cavity optionally produced therein (as discussed below). When the sample holder produced in this manner is placed within the sample holder base it is relatively immobile because of the snug fit. Alternatively, however, any size or shape flat plate of silicon which is small enough to fit in the base may be utilized provided said plate is effective in holding a specimen for analysis and it is firmly attached to the base in the desired location with a conventional fastening means such as a glue or adhesive.

Figure 2:
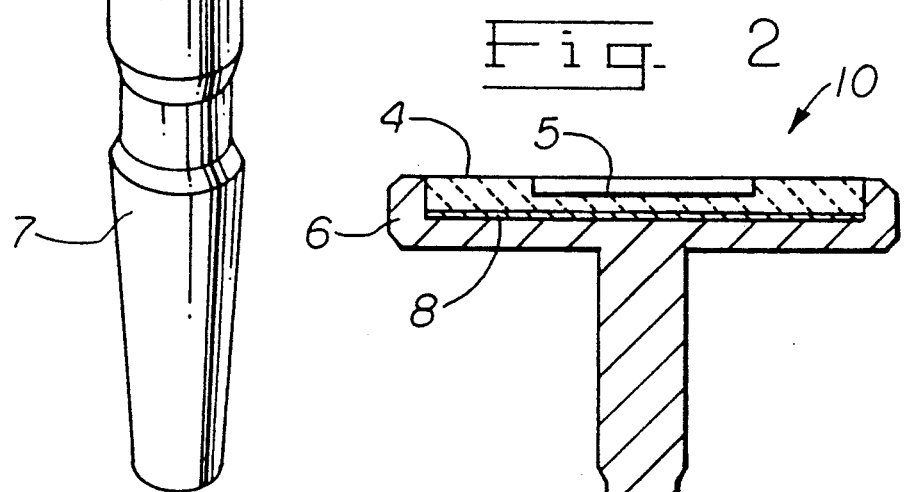
FIG. 2 is a cross-sectional view of FIG. 1.

The thickness of the silicon wafer (slice) from which the sample holder is cut is important to insure that the x-ray beams of the diffractometer focus appropriately on the powder specimen. Again, the desired thickness of the sample holder will vary depending on the base but for that described in FIG. 1 it should be approximately 0.043 inches thick such that the upper surface of the holder (4) is flush with the top edge of said base. This thickness may be achieved by the use of a single crystal silicon wafer of the appropriate thickness, two or more silicon wafers may be combined to achieve the desired thickness, or a shim may be added to a silicon wafer or wafers to increase the thickness. If a shim is used, it can be made of any convenient material such as glass, a ceramic, metal, etc. FIG. 2 shows a cross section of a sample holder of this invention (10) as a single slice of single crystal silicon grown in the [100] direction with a shim (8) added to increase the thickness of the sample holder so the top of the sample holder (4) is flush with the top of the sample holder base (6).

In one embodiment of this invention no cavity is produced in the silicon sample holder (not shown in a figure) such that the invention merely comprises a flat plate or disk of silicon in which the upper surface is approximately flush with the upper edge of the sample holder base. This embodiment is particularly advantageous for analyzing thin films of a material Which do not require containment.

In a preferred embodiment of this invention there is a cavity (5) in the sample holder to hold and contain a powder specimen. The size, shape and location of this cavity may vary depending on the sample holder base but it should be one which is suitable to hold the specimen in a position which allows the diffractometer to analyze it. For the sample holder of FIG. 1, a circular cavity with its center at the center of the holder base is generally utilized. Preferably, the cavity has a diameter in the range of about 0.25 to 0.75 inches to allow adequate focusing with a diameter of about 0.5 inches being more preferred. The depth of this cavity, likewise, may vary but depths in the range of about 0.005 to about 0.030 inches are often used. Larger and deeper cavities may be used but such cavities also require the use of larger amounts of specimen. This cavity may be formed in the sample holder by any appropriate means known in the art such as machining or as described below.

Figure 3:
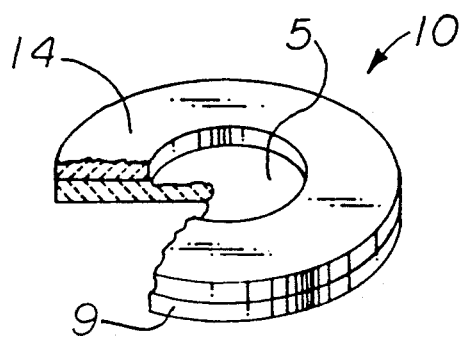
FIG. 3 is a partial perspective view of a preferred embodiment of the sample holder of this invention.

In the most preferred embodiment of this invention the sample holder has the configuration shown in FIG. 3. In manufacturing this embodiment, 2 circular disks, with a diameter of about 1 inch (disk 9 and disk 14) are cut from 0.015 inch or 0.025 inch thick single crystal silicon wafers. Preferably, two 0.015 inch thick wafers are used. A circular hole of the size needed for the sample cavity (5) is then cut into the center of disk 14 (i.e., about 0.5 inches in diameter). The disks are then aligned on top of each other as shown in FIG. 3 and fastened together by a conventional fastening means such as a glue or an adhesive (e.g. an epoxy, SUPER GLUE TM, etc.). In this manner, a circular sample holder (10) approximately 1 inch in diameter and about 0.03 inches (2×0.015) thick is formed. In the center of this holder is a circular cavity (5) (formed by the hole bored into disk 14) for holding the specimen. Since this holder is not sufficiently thick for the base, a glass shim is added to increase the total thickness to about 0.043 inches.

Since the sample holder of this invention is constructed from single crystal silicon, there is very little background (because it is a single crystal) and the diffraction peak that may be produced is in a location on the diffraction pattern which does not interfere with interpretation of the results (69°, 2-theta). In fact, this peak may be valuable as a reference for absorption correction. In addition, since the single crystal silicon has a polished surface it is very easy to clean and maintain. Finally, single crystal silicon is a relatively inexpensive material such that the sample holder can be manufactured in a cost effective manner.

The following non-limiting example is provided so that one skilled in the art will more fully understand the invention.

EXAMPLE

A sample holder was manufactured as follows: 2 circular disks with a diameter of about 1 inch were cut from a 0.015 inch thick single crystal silicon wafer. A circular hole with a diameter of about 0.5 inches was then cut into the center of one of the disks. The disks were then aligned on top of each other and fastened together with SUPER GLUE TM. A glass shim about 0.013inches thick was glued (with SUPER GLUE TM) to the bottom of the bottom disk to increase the total thickness to about 0.043 inches.

This holder was then evaluated against commercially available aluminum and quartz holders both when empty (Table 1) and when filled with silicon carbide and trace carbon (Table 2). The evaluation was performed on a Phillips TM x-ray powder diffractometer and the results are provided in the following tables.

TABLE 1

Empty Holder

| | Background Peak Height (mm) | | | | | Holder Peak $\frac{2 - \theta°}{\text{height-mm}}$ | | | |
|---|---|---|---|---|---|---|---|---|---|
| | 10° | 20° | 30–40° | 50–60° | 70–80° | 1 | 2 | 3 | 4 |
| Al | 11 | 5 | 4–5 | 3.0–2.5 | 2.5–3.5 | $\frac{38.2}{417}$ | $\frac{44.4}{449}$ | $\frac{65.0}{105}$ | $\frac{78.1}{132}$ |
| Quartz | 8.5 | 2.5 | 1–0 | 0–0 | 0–0 | $\frac{16.2}{5}$ | $\frac{50.5}{7}$ | | |
| Silicon | 9 | 3 | 1–0 | 0–0 | 0–0 | $\frac{32.8}{40}$ | $\frac{69.0}{533}$ | | |

TABLE 2

| | Holder Filled with SiC and C | | | | | | | | |
|---|---|---|---|---|---|---|---|---|---|
| | Background Peak Height (mm) | | Sample Peaks $\frac{2-\theta°}{ht(mm)}$ | | | Holder Peak $\frac{2-\theta°}{ht(mm)}$ | | | |
| | 10–30° | 40–80° | max | min | trace | 1 | 2 | 3 | 4 |
| Al | 9–2 | 1–0.5 | $\frac{35.9}{260}$ | $\frac{75.7}{10}$ | — | $\frac{38.5}{87}$ | $\frac{44.7}{89}$ | $\frac{65.1}{12}$ | $\frac{78.2}{12}$ |
| Quartz | 9–2 | 1–0.5 | $\frac{35.9}{265}$ | $\frac{75.7}{11}$ | $\frac{26.2}{2}$ | $\frac{50.6}{6}$ | | | |
| Silicon | 9–2 | 1–0.5 | $\frac{35.7}{300}$ | $\frac{75.5}{12}$ | $\frac{26.2}{2}$ | $\frac{69.1}{6}$ | | | |

That which is claimed is:

1. An x-ray powder diffractometer sample holder wherein the improvement comprises:
    said holder being manufactured from single crystal silicon grown in the [100] direction.

2. The x-ray powder diffractometer sample holder of claim 1 wherein said holder has a cavity therein to hold a powder sample.

3. A sample holder for an x-ray powder diffractometer, the holder comprising:
    a flat plate made of single crystal silicon grown in the [100] direction having an upper surface and a lower surface, wherein the flat plate has a size and shape such that the lower surface fits into a conventional sample holder base and the upper surface of the holder is flush with the upper edge of the sample holder base.

4. The sample holder of claim 3 wherein the flat plate comprises a disk.

5. The sample holder of claim 3 wherein the flat plate comprises two or more slices of single crystal silicon.

6. The sample holder of claim 3 wherein the flat plate comprises one or more slices of single crystal silicon and a shim.

7. A sample holder for an x-ray powder diffractometer, the holder comprising:
    a top flat plate made of single crystal silicon grown in the [100] direction, the top flat plate containing an opening therethrough to outline a cavity for holding a powder sample and
    a bottom flat plate having a size sufficient to cover the opening in the top flat plate, the bottom flat plate being aligned under the top flat plate to cover the opening in the top flat plate and being held to the bottom side of the top flat plate by a fastening means.

8. An x-ray powder diffractometer sample holder comprising;
    2 disks having approximately the same diameter made of single crystal silicon grown in the [100] direction,
    wherein the disks comprise a top disk and a bottom disk each having a top side and a bottom side.
    wherein the disks are aligned on top of each other and placed in direct contact therewith such that the bottom side of the top disk is directly aligned over the top side of the bottom disk and the disks are held together by a fastening means, and
    wherein the size and combined thickness of said disks is such that they fit within a base of a sample holder for an x-ray powder diffractometer.

9. The sample holder of claim 8 wherein the top disk has a hole in the center thereof to outline a sample cavity size.

10. The sample holder of claim 8 wherein the disks each have a diameter of less than about 1 inch.

11. The sample holder of claim 8 wherein the disks each have a diameter of about 1 inch.

12. The sample holder of claim 9 wherein the hole in the top disk has a diameter in the range of about 0.25 to 0.75 inch.

13. The sample holder of claim 12 wherein the hole in the top disk has a diameter of about 0.5 inch.

14. The sample holder of claim B wherein the disks have a thickness selected from the group consisting of 0.015 inches and 0.025 inches.

15. The sample holder of claim 9 wherein the disks have a thickness selected from the group consisting of 0.015 inches and 0.025 inches.

16. The sample holder of claim 15 wherein each disk is 0.015 inches thick.

17. The sample holder of claim 8 further comprising a shim applied to the bottom side of the bottom disk such that the total thickness of the sample holder is about 0.043 inch.

18. The sample holder of claim 16 further comprising a shim applied to the bottom side of the bottom disk such that the total thickness of the sample holder is about 0.043 inch.

* * * * *

UNITED STATES PATENT AND TRADEMARK OFFICE
CERTIFICATE OF CORRECTION

PATENT NO. : 5,084,910

DATED : January 28, 1992

INVENTOR(S) : William R. Albe, et al

It is certified that error appears in the above-indentified patent and that said Letters Patent is hereby corrected as shown below:

Title page, item [73] Assignee:  should read
            --Dow Corning Corporation, Midland, Michigan.--

Signed and Sealed this

Thirteenth Day of July, 1993

Attest:

MICHAEL K. KIRK

Attesting Officer

Acting Commissioner of Patents and Trademarks